United States Patent [19]

Nakagawa et al.

[11] 4,065,456
[45] Dec. 27, 1977

[54] GLYCEROL DERIVATIVES OF QUINOLINE CARBOSTYRYL AND ISOCARBO STYRYL

[75] Inventors: Kazuyuki Nakagawa; Nanami Murakami; Hideo Mori; Kaoru Tanimura, all of Tokushima, Japan

[73] Assignee: Otsuka Pharmaceutical Co., Ltd., Tokyo, Japan

[21] Appl. No.: 517,730

[22] Filed: Oct. 24, 1974

[30] Foreign Application Priority Data

Oct. 24, 1973 Japan .............................. 48-120237
Oct. 26, 1973 Japan .............................. 48-120994
Aug. 7, 1974 Japan .............................. 49-90985
Aug. 7, 1974 Japan .............................. 49-90986

[51] Int. Cl.² .................. C07D 215/22; C07D 217/24
[52] U.S. Cl. .......................... 260/289 R; 260/289 D; 260/289 K; 260/345.2; 260/590 FA; 424/258
[58] Field of Search ........... 260/289 R, 289 D, 289 R

[56] References Cited

U.S. PATENT DOCUMENTS 2,448,767  9/1948  Carlson ........................... 260/289 R
3,424,681  1/1969  Stanford .......................... 260/289 R
3,862,951  1/1975  Gottwald et al. ............... 260/289 R

*Primary Examiner*—Alton D. Rollins
*Assistant Examiner*—D. B. Springer
*Attorney, Agent, or Firm*—Sughrue, Rothwell, Mion, Zinn and Macpeak

[57] ABSTRACT

A glycerol derivative represented by the formula (I)

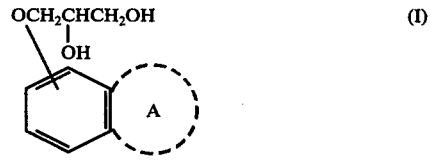

wherein A is hereinafter defined, including the optically active isomers per se and mixtures of the optically active isomers, which are useful as a central nervous system depressant, an intermediate for the preparation of β-adrenergic blocking agents, an inhibitor of blood platelet aggregation or a choleretic agent, and a process for preparing the above glycerol derivative.

28 Claims, No Drawings

GLYCEROL DERIVATIVES OF QUINOLINE CARBOSTYRYL AND ISOCARBO STYRYL

BACKGROUND OF THE INVENTION

1. Field of the Invention

This invention relates to glycerol derivatives and a process for preparing the same. More particularly this invention relates to glycerol derivatives having the formula (I) as described herein which are useful as a central nervous system depressant, intermediates for the preparation of β-adrenergic blocking agents, as an inhibitor of platelet aggregation and as a choleretic agent.

2. Description of the Prior Art

It is well known that certain glycerol derivatives can be used as a metabolic intermediate of β-adrenergic blocking agents. For example, *Drug Metabolism Review*, Vol. I(1), 101–116 (1972) discloses 1-(2,3-dihydroxy)-propoxynaphthalene as a metabolic intermediate. However, the pharmacological activities of these glycerol derivatives have not yet been studied in detail.

Compounds which are known as platelet aggregation inhibitors include nucleic acid (xanthine) derivatives, prostaglandines, 1,3-diphenadions (e.g., as disclosed in U.S. Pat. No. 2,672,483), but it is not known that glycerol derivatives exhibit an inhibitory activity on platelet aggregation.

SUMMARY OF THE INVENTION

An object of the present invention is to provide glycerol derivatives including the optically active isomers thereof which are useful as a central nervous system depressant, an intermediate for β-adrenergic blocking agents, a platelet aggregation inhibitor or a choleretic agent.

Another object of this invention is to provide a process for the preparation of the above-described glycerol derivatives.

A further object of this invention is to provide a pharmaceutical composition comprising at least one of the above-glycerol derivatives.

This invention accordingly provides a glycerol derivative of the general formula (I)

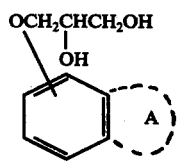
(I)

including the optically active isomers thereof, wherein the ring A represents a substituted or unsubstituted 5- or 6-membered heterocyclic ring containing 1 or 2 oxygen atoms or nitrogen atoms or a substituted or unsubstituted 5- or 6-membered alicyclic ring, and a process for preparing the same.

DETAILED DESCRIPTION OF THE INVENTION

The glycerol derivatives according to the present invention of the general formula (I) have been found not only to be useful as the hereinbefore-described intermediates for the synthesis of β-adrenergic blocking agents but also to have, per se, an inhibitory activity on platelet aggregation.

The glycerol derivatives of the present invention are, therefore, of value as a new type of platelet aggregation inhibitors. In addition, it has been found that some of the glycerol derivatives of this invention have a choleretic activity.

Typical examples of the ring A in the formula (I) above can be represented by the following structures:

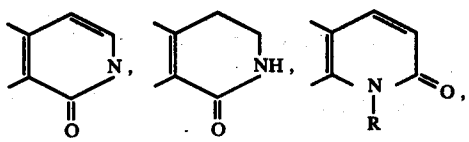

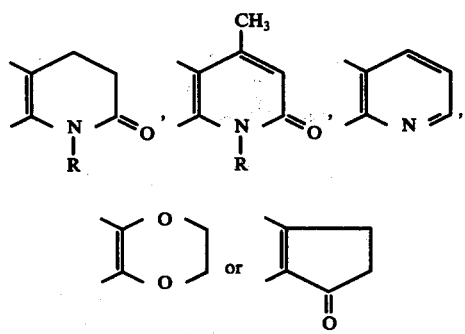

wherein R represents a hydrogen atom, an alkyl group, an alkenyl group or an aralkyl group.

Particularly preferred examples of A are

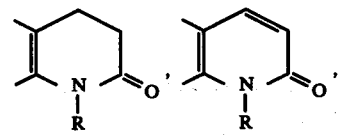

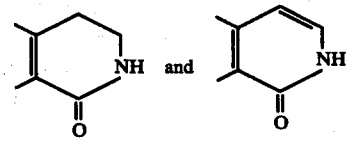

wherein R is as defined above, which form, together with the benzene ring, a carbostyril or 3,4-dihydrocarbostyril structure or an isocarbostyril or 3,4-dihydroisocarbostyril structure.

The term "alkyl group" as used herein designates a straight or branched chain alkyl group having 1 to 4 carbon atoms, e.g., a methyl, ethyl, isopropyl, butyl or the like group.

The term "alkenyl group" as used herein designates an alkenyl group having 2 to 4 carbon atoms, e.g., a vinyl, allyl, propenyl, butenyl or the like group.

The term "aralkyl group" as used herein designates a phenylalkyl group having 1 or 2 carbon atoms in the alkyl moiety, e.g., a benzyl or phenethyl group.

The glycerol derivatives represented by the formula (I) of this invention can be prepared by various processes.

The glycerol derivatives represented by the formula (I)

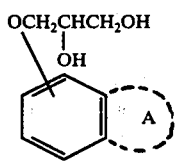 (I)

wherein A is as defined above can be prepared by reacting the corresponding hydroxy compound represented by the formula (II)

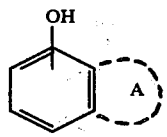 (II)

wherein A is as defined above, with a compound represented by the formula (III)

Y—CH₂OH  (III)

wherein Y is a

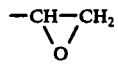

group or a

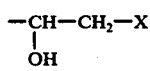

group wherein X represents a halogen atom such as chlorine, bromine and iodine, in the presence of a basic compound as an acid acceptor.

The compound of the formula (II) which can be used in the above process includes:

i. 1-substituted or unsubstituted-5, 6, 7 or 8-hydroxycarbostyrils having the formula (IIa)

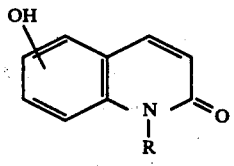 (IIa)

wherein R is as defined above, and the 4-methyl substituted analogues of these compounds;

ii. 1-substituted or unsubstituted-5, 6, 7 or 8-hydroxy-3,4-dihydrocarbostyrils having the formula (IIb)

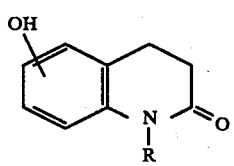 (IIb)

wherein R is as defined above;

iii. 5, 6, 7 or 8-hydroxyisocarbostyrils having the formula (IIc);

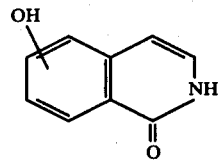 (IIc)

iv. 5, 6, 7 or 8-hydroxy-3,4-dihydroisocarbostyrils having the formula (IId):

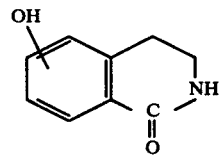 (IId)

v. 5, 6, 7 or 8-hydroxyquinolines having the formula (IIe);

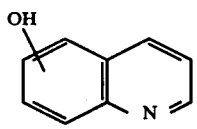 (IIe)

vi. 5, 6, 7 or 8-hydroxy-1,4-benzodioxanes having the formula (IIf);

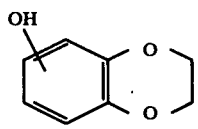 (IIf)

or vii. 4, 5, 6, or 7-hydroxyhydroinden-1-ones having the formula (IIg).

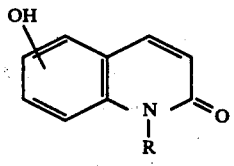 (IIg)

These compounds as described above are well known in the art. For example, 5-hydroxy-3,4-dihydrocarbostyril is disclosed in Japanese Patent Publication No. 38789/71 and in *Chemistry and Industry*, 1435 (1970); 8-hydroxycarbostyril is disclosed in *J. Org. Chem.*, 36, (23), 3490-3 (1971); 7-hydroxyindanone is disclosed in *J. Chem. Soc.*, 1954, 4299 and 5-hydroxyisocarbostyril is disclosed in *J. Am. Chem. Soc.*, 69, 1939 (1947).

The compounds represented by the formula (III) which can be used in the above reaction include glycerol β-halohydrins, wherein the halogen atom can be a chlorine, bromine or iodine atom, and glycidol.

The reaction between the compound (II) and the compound (III) can be carried out in the presence of a basic compound as an acid acceptor. Acid acceptors found to be useful in the reaction include any basic compounds, such as alkali metals, alkali metal hydroxides, alkali metal carbonates, alkali metal alkoxides organic bases and the like, but sodium metal, potassium metal, sodium hydroxide, potassium hydroxide, sodium carbonate, potassium carbonate, sodium alcoholate, potassium alcoholate or piperidine, piperazine, pyridine, lower alkylamines, e.g., diethylamine, triethylamine, methylamine, etc. are preferably used. These basic compounds can be employed in a molar ratio of from about 0.5 to about 2 moles, preferably in an approximately equimolar proportion with respect to the compound (II).

Generally, the above described reaction can advantageously be carried out using approximately equimolar amounts of the compounds (II) and (III), but use of an excessive amount of either of these reactants does not adversely affect the reaction. It is usually preferable to use about 1 to 5 moles of the compound (III) per 1 mole of the compound (II).

This reaction can be carried out at atmospheric pressure (elevated pressures can also be used if desired) in the presence of an acid acceptor in the presence or absence of a solvent, for example, such as a lower alkanol, water, a lower alkyl acetate and a ketone. Suitable examples of lower alkanols are methanol, ethanol, isopropanol, n-propanol, n-butanol and the like. Suitable examples of lower alkyl acetates are ethyl acetate, methyl acetate propyl acetate and the like. Suitable examples of ketones are acetone and methyl ethyl ketone. When a solvent is used, the concentration of the reactants in these solvents can be preferably from about 10% to about 30% by weight. It is preferred to select the solvent depending upon the type of acid acceptor used. For example, in a preferred embodiment, lower alkanols are used with alkali metals and water is used with alkali metal hydroxides. When the acid acceptors used are organic bases as set forth above, the reaction can be carried out in the absence of a solvent or using a lower alkanol, a lower alkyl acetate and a ketone as a solvent.

The reaction temperature ranges from about 0° to about 150° C, preferably 50° to 100° C. The reaction time will vary depending upon the temperature and the type of the reactants employed, but usually ranges from about 1 to 10 hours. In a preferred embodiment, the reaction can be carried out for 2 to 5 hours at the reflux temperature of the solvent used.

The reaction product thus obtained can be isolated as crystals in a usual manner or further purified by, for example, recrystallization and the like. In a typical technique for isolation of the reaction product, the reaction mixture is filtered while warm to remove insoluble substances, and the filtrate is either cooled to precipitate crystals, which are then separated by filtration, decantation, etc. or the above filtrate is concentrated to dryness and the residue is either recrystallized from water, ethyl acetate or the above enumerated alcohols or extracted with chloroform and the like and the extract is dried and concentrated thereby isolating the product.

Alternatively, the compound of the formula (I) according to the present invention can also be prepared by reacting the hydroxy compound of the formula (II) with an epihalohydrin such as epichlorohydrin, epibromohydrin and the like in the presence of an appropriate acid acceptor to produce a compound having the formula (IVa) or (IVb)

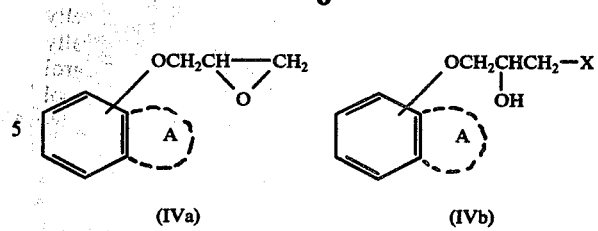

wherein R and X are as defined above, and hydrolyzing the resulting compound, particularly preferably under basic conditions.

The reaction between the hydroxy compound (II) and the epihalohyrin can be carried out in the presence of an acid acceptor in the presence or absence of a solvent. Suitable examples of acid acceptors and solvents which can be used are those enumerated above for the reaction between the hydroxy compound (II) and glycerol α-halohydrin or glycidol. The reaction temperature can range from about 0° to about 120° C, preferably from 50° C to 100° C. The reaction can be carried out by using the epihalohydrin in an amount of from about 1 to 5, preferably 3 to 4, moles per 1 mole of the hydroxy compound (II) and the reaction time generally ranges from about 2 to about 8 hours, more generally from 4 to 5 hours.

The subsequent hydrolysis of the compound represented by the formula (IVa) or (IVb) can be effected in the presence of a basic compound as set forth above at a temperature of about 0° to 150° C, preferably 60° to 100° C for a period of from about 1 to 10 hours. A solvent such as those enumerated above can be advantageously used in the hydrolysis.

Alternatively, the hydrolysis can be effected with an aqueous solution of an acid such as inorganic acids, for example, sulfuric acid, hydrochloric acid, phosphoric acid or perhalic acids, for example, perchloric acid having an acid concentration of from about 5% to about 20% by weight. The acid hydrolysis can be carried out at a temperature of from about 0° to about 100° C, preferably from 20° to 50° C for a period of from about 1 to about 8 hours, preferably from 3 to 6 hours.

The compounds represented by the formula (I) of the present invention can also be prepared by the following reaction scheme:

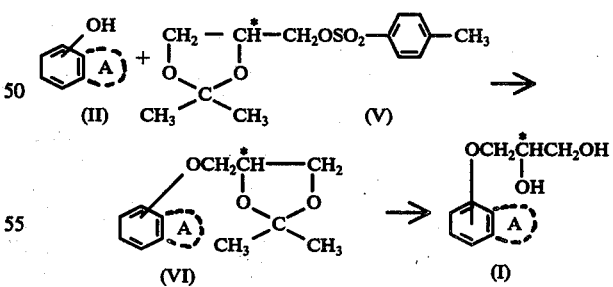

wherein A and R are as defined above.

In the above reaction, a 5, 6, 7 or 8-hydroxy compound represented by the formula (II) is reacted with a glycerol derivative (V) in the presence of a basic compound to produce the acetone glycerol (VI) corresponding to the hydroxy compound (II), which is then hydrolyzed to obtain the desired product of the formula (I).

As is understood by those skilled in the art, the glycerol derivative (V) above contains one asymmetric center indicated by the asterisk * and is, therefore, optically active. Thus, in this reaction, depending on the optically active (R)-(−)-α-(p-toluenesulfonyl)-acetone glycerol (V) or (S)-(+)-α-(p-toluenesulfonyl)-acetone glycerol (V) isomer used, the corresponding (S)-(+)- or (R)-(−)-acetone glycerol, respectively, can be formed which is then hydrolyzed to prepare a glycerol derivative (I) as predominately an optically active R-(−)-glycerol (I) or (S)-(+)-glycerol (I) form. Such a process is quite advantageous where a particular optically active glycerol derivative (I) is desired over the other processes disclosed herein where a mixture of optically active glycerol derivative (I) is obtained.

The optically active glycerol derivatives (V) which can be used in the above reaction scheme can be prepared according to the methods described in E. Bear, *J. Am. Chem. Soc.*, 67, 338 (1945), E. Bear, H. O. L. Fischer, *J. Biol. Chem.*, 128, 463 (1939) and ibid, and *J. Am. Chem. Soc.*, 70, 609 (1948).

The reaction between the 5, 6, 7 or 8-hydroxy compound (II) and the optically active glycerol derivative (V) can be carried out in the presence of a basic compound such as those enumerated for the reaction between the compound (II) and the compound (III), in a molar ratio of from about 1 to 3 moles of the optically active glycerol derivative (V) per mole of the 5, 6, 7 or 8-hydroxy compound (II), preferably using approximately equimolar amounts of the reactants, at a temperature of about 50° to 250° C, preferably 80° to 150° C. Solvents such as an alkanol having 1 to 4 carbon atoms e.g., methanol, ethanol, isopropanol, butanol and the like, 2-methoxyethanol, dioxane, dimethylformamide, acetonitrile and the like can be employed in the reaction.

The hydrolysis of the acetone glycerol of the general formula (VI) can be in an aqueous solution of a hydrolyzing agent such as acetic acid, trifluoro-acetic acid, hydrochloric acid, sulfuric acid, etc. at a temperature of about 0° C to 100° C for 10 minutes to 2 hours.

The present invention is further illustrated by the following Examples but these Examples are not to be construed as limiting the scope of this invention. Unless otherwise indicated, all parts, percentages, ratios and the like are by weight.

EXAMPLE 1

0.23 g of sodium metal was dissolved in 40 ml of methanol, and 2.53 g of 1-benzyl-5-hydroxy-3,4-dihydrocarbostyril and 1.3 g of glycerol α-monochlorohydrin were added to the resulting solution followed by refluxing the mixture for 6 hours. After allowing the mixture to cool, the precipitated crystals were filtered, and the filtrate was concentrated to dryness. The residue thus obtained was extracted with 50 ml of chloroform, and the extract was washed with a 5% aqueous sodium hydroxide solution and then water and then dried over anhydrous sodium sulfate. The chloroform was then removed by distillation and the resulting residue was recrystallized from ethanol to give 1.2 g of 1-benzyl-5-(2,3-dihydroxy)propoxy-3,4-dihydrocarbostyril as a colorless amorphous solid having a melting point of 153° – 155° C.

EXAMPLE 2

2.0 g of potassium hydroxide was dissolved in 80 ml of methanol, and 4.8 g of 1-methyl-5-hydroxy-3,4-dihydrocarbostyril and 4.0 g of glycerol α-monochlorohydrin were added to the resulting solution followed by refluxing the mixture for 4 hours. After allowing the mixture to cool, the precipitated crystals were filtered, and the filtrate was concentrated to dryness. The residue thus obtained was extracted with 120 ml of chloroform, and the extract was washed with a 5% aqueous potassium hydroxide solution and then water and then dried over anhydrous sodium sulfate. The chloroform was then removed by distillation and the resulting residue was recrystallized from ethyl acetate to give 1.5 g of 1-methyl-5-(2,3-dihydroxy)propoxy-3,4-dihydrocarbostyril as a colorless amorphous solid having a melting point of 120° – 121° C.

EXAMPLE 3

2.0 g of potassium hydroxide was dissolved in 80 ml of methanol, and 5.2 g of 1-ethyl-5-hydroxy-3,4-dihydrocarbostyril and 5.0 g of glycerol α-bromohydrin were added to the resulting solution followed by refluxing the mixture for 4 hours. The mixture was then worked up in the same manner as described in Example 1 to obtain a residue after removal of the chloroform by distillation. The residue thus obtained was recrystallized from ethyl acetate to give 1.9 g of 1-ethyl-5-(2,3-dihydroxy)propoxy-3,4-dihydrocarbostyril as a colorless amorphous solid having a melting point of 105° – 107° C.

EXAMPLE 4

0.4 g of potassium hydroxide was dissolved in 40 ml of methanol, and 1.0 g of 1-allyl-5-hydroxy-3,4-dihydrocarbostyril and 1.5 g of glycerol α-monochlorohydrin were added to the resulting solution followed by refluxing the mixture for 6 hours. The mixture was then worked up in the same manner as described in Example 3 and recrystallized from ethyl acetate to give 0.6 g of 1-allyl-5-(2,3-dihydroxy)propoxy-3,4-dihydrocarbostyril as a colorless amorphous solid having a melting point of 96° – 97.5° C.

EXAMPLE 5

0.23 g of sodium metal was dissolved in 40 ml of ethanol, and 1.63 g of 5-hydroxy-3,4-dihydrocarbostyril and 1.1 g of glycerol α-monochlorohydrin were added to the resulting solution followed by refluxing the mixture for 6 hours. After allowing the mixture to cool, the precipitated crystals were filtered, and the filtrate was concentrated to dryness. The residue thus obtained was extracted with 100 ml of chloroform, and the extract was washed with a 5% aqueous sodium hydroxide solution and then water and then dried over anhydrous sodium sulfate. The chloroform was then removed by distillation and the resulting residue was recrystallized from ethanol to give 0.7 g of 5-(2,3-dihyroxy)propoxy-3,4-dihydrocarbostyril as a colorless amorphous solid having a melting point of 173° – 175° C.

EXAMPLE 6

0.7 g of potassium hydroxide was dissolved in 30 ml of methanol, and 2.5 g of 1-benzyl-5-hydroxy-3,4-dihydrocarbostyril and 0.9 g of glycidol were added to the resulting solution followed by refluxing the mixture for 4 hours. After the mixture was concentrated to dryness, the residue was extracted with 50 ml of chloroform, and the extract was washed with a 5% aqueous potassium hydroxide and then water and then dried over anhydrous sodium sulfate. The chloroform was then removed by distillation and the resulting residue was recrystallized from ethyl acetate to give 1.4 g of 1-benzyl-5-(2,3-dihydroxy)propoxy-3,4-dihydrocarbostyril as colorless needle-like crystals having a melting point of 154° – 155° C.

EXAMPLE 7

0.8 g of potassium hydroxide was dissolved in 50 ml of methanol, and 1.63 g of 8-hydroxy-3,4-dihydrocarbostyril and 1.4 g of glycerol α-monochlorohydrin were added to the resulting solution followed by refluxing the mixture for 3 hours. The raction mixture was then concentrated to dryness, and the resulting residue was extracted with 50 ml of chloroform. The extract was washed with a 2% aqueous sodium hydroxide solution and then water, and then dried over anhydrous sodium sulfate. The chloroform was then removed by distillation and the resulting residue was recrystallized from ethanol to give 0.8 g of 8-(2,3-dihydroxy)propoxy-3,4-dihydrocarbostyril as a light yellow amorphous solid having a melting point of 182° – 184° C.

EXAMPLE 8

In the same manner as described in Example 7, 6-hydroxy-3,4-dihydrocarbostyril was reacted with gylcerol α-monochlorohydrin to give 6-(2,3-dihydroxy)-propoxy-3,4-dihydrocarbostyril as white needle-like crystals having a melting point of 190° – 192° C.

EXAMPLE 9

In the same manner as described in Example 7, 7-hydroxy-3,4-dihydrocarbostyril was reacted with glycerol α-monochlorohydrin to give 7-(2,3-dihydroxy)-propoxy-3,4-dihyrocarbostyril as white needle-like srystals having a melting point of 143° – 144° C.

EXAMPLE 10

1.0 g of sodium hydroxide was dissolved in 20 ml of water, and 1.0 g of 1-benzyl-5-(2,3-epoxy)propoxy-3,4-dihydrocarbostyril was added to the resulting solution followed by stirring the mixture at a temperature of 80° to 85° C for 6 hours. The reaction mixture was then filtered while hot to remove any insoluble materials, and the filtrate was cooled. The precipitated crystals were filtered and dried, and recrystallized from ethyl acetate to give 0.4 g of 1-benzyl-5-(2,3-dihydroxy)-propoxy-3,4-dihydrocarbostyril as colorless needle-like crystals having a melting point of 154° – 155° C.

EXAMPLE 11

1.5 g of potassium hydroxide was dissolved in 30 ml of water, and 1.2 g of 1-methyl-5-(2,3-epoxy)propoxy-3,4-dihydrocarbostyril was added to the resulting solution followed by stirring the mixture at a temperature of 80° to 90° C for 8 hours. The reaction mixture was then filtered while hot to remove any insoluble materials, and the filtrate was cooled. The precipitated crystals were filtered and dried, and recrystallized from ethyl acetate to give 0.5 g of 1-methyl-5-(2,3-dihydroxy)-propoxy-3,4-dihydrocarbostyril as a colorless amorphous solid having a melting point of 120° – 121° C.

EXAMPLE 12

0.5 g of sodium hydroxide was dissolved in 10 ml of water, and 1.0 g of 5-(2,3-epoxy)propoxy-3,4-dihydrocarbostyril was added to the resulting solution followed by stirring the mixture at a temperature of 75° to 80° C for 3 hours. The reaction mixture was then concentrated to dryness, and the resulting residue was recrystallized from water to give 0.55 g of 5-(2,3-dihydroxy)propoxy-3,4-dihydrocarbostyril as a colorless amorphous solid having a melting point of 173° – 175° C.

EXAMPLE 13

0.5 g of sodium hydroxide was dissolved in 10 ml of water, and 1.1 g of 5-(3-chloro-2-hydroxy)propoxy-3,4-dihydrocarbostyril was added to the resulting solution followed by stirring the mixture at a temperature of 75° to 80° C for 5 hours. The reaction mixture was then concentrated to dryness, and the resulting residue was recrystallized from ethanol to give 0.42 g of 5-(2,3-dihydroxy)propoxy-3,4-dihydrocarbostyril as a colorless amorphous solid having a melting point of 173° – 174° C.

Following the procedure described in Examples 10 to 13, the following compounds were prepared:

1-Ethyl-5-(2,3-dihydroxy)propoxy-3,4-dihydrocarbostyril as white needle-like crystals having a melting point of 105° – 107° C after recrystallization from ethyl acetate, 1-Allyl-5-(2,3-dihydroxy)propoxy-3,4-dihydrocarbostyril as white needle-like crystals having a melting point of 96° – 98° C after recrystallization from ethyl acetate, 8-(2,3-Dihydroxy)propoxy-3,4-dihydrocarbostyril as white needle-like crystals having a melting point of 182° – 184° C after recrystallization from ethanol, 6-(2,3-Dihydroxy)propoxy-3,4-dihydrocarbostyril as white needle-like crystals having a melting point of 190° – 192° C after recrystallization from ethanol, and 7-(2,3-Dihydroxy)propoxy-3,4-dihydrocarbostyril as white needle-like crystals having a melting point of 143° – 144° C after recrystallization from ethanol.

REFERENCE EXAMPLE 1

0.34 g of 5-hydroxy-3,4-dihydrocarbostyril and 0.15 g of sodium ethylate were added to 34 ml of 2-methoxyethanol, and the mixture was refluxed for 10 minutes. To the resulting mixture was then added a solution of 0.6 g of (R)-(−)-α-(p-toluenesulfonyl)acetone glycerol dissolved in 6 ml of 2-methoxyethanol, and the mixture was refluxed for 3 hours. After allowing the mixture to stand overnight at room temperature (about 20° – 30° C), the solvent was distilled off under reduced pressure. The residue thus obtained was extracted with 100 ml of chloroform, and the extract was washed with 1N sodium hydroxide and then water and then dried over anhydrous sodium sulfate. The chloroform was then removed by distillation, and the residue was recrystallized from methanol to give 0.35 g of (S)-(+)-α-(3,4-dihydro-5-carbostyril)acetone glycerol as white crystals having a melting point of 171° – 173° C and $[\alpha]_D^{22} = +24.6°$ (c=0.8, CHCl$_3$).

REFERENCE EXAMPLE 2

0.68 g of 5-hydroxy-3,4-dihydrocarbostyril and 0.35 g of potassium ethylate were added to 7.0 ml of 2-methoxyethanol, and the mixture was refluxed for 10 minutes. To the resulting mixture was then added a solution of 1.2 g of (S)-(+)-α-(p-toluenesulfonyl)acetone glycerol dissolved in 12 ml of 2-methoxyethanol, and the mixture was refluxed for 3 hours. The reaction mixture was then worked up in the same manner as described in Reference Example 1 to give 0.67 g of (R)-(−)-α-(3,4-dihydro-5-carbostyril)acetone glycerol as white crystals having a melting point of 171° – 172° C and $[\alpha]_D^{22} = -24.5°$ (c=0.8, CHCl$_3$).

EXAMPLE 14

9 ml of an 80% acetic acid aqueous solution was added to 0.9 g of (S)-(+)-α-(3,4-dihydro-5-carbostyril)acetone glycerol, and the mixture was heated at a bath temperature of 55° to 60° C for 30 minutes. After allowing the mixture to cool, 135 ml of diethyl ether was added to the mixture followed by cooling, and the precipitated crystals were filtered and recrystallized from ethanol to give 0.5 g of (R)-(−)-α-(3,4-dihydro-5-carbostyril)-glycerol as white crystals having a melting point of 191° − 192° C and $[\alpha]_D^{23} = -5.4°$ (c=0.4, pyridine).

EXAMPLE 15

5 ml of an 80% acetic acid aqueous solution was added to 0.5 g of (R)-(−)-α-(3,4-dihydro-5-carbostyril)acetone glycerol, and the mixture was heated at a bath temperature of 60° − 65° C for 30 minutes. After allowing the mixture to cool, 100 ml of diethyl ether was added to the mixture followed by cooling, and the precipitated crystals were filtered and recrystallized from ethanol to give 0.3 g of (S)-(+)-α-(3,4-dihydro-5-carbostyril)glycerol as white crystals having a melting point of 191° − 192° C and $[\alpha]_D^{23} = +5.4$ (c=0.4, pyridine).

REFERENCE EXAMPLE 3

1.8 g of 6-hydroxy-3,4-dihydrocarbostyril and 0.7 g of sodium ethylate were added to 9 ml of 2-methoxyethanol, and the mixture was refluxed for 10 minutes. To the resulting mixture was then added a solution of 3.0 g of (R)-(−)-α-(p-toluenesulfonyl)acetone glycerol dissolved in 6 ml of 2-methoxyethanol, and the mixture was refluxed for 3 hours. After allowing the mixture to cool, the solvent was distilled off under reduced pressure. The residue thus obtained was shaken with 100 ml of chloroform and 100 ml of a 1N sodium hydroxide aqueous solution, and the organic layer was separated, washed with 100 ml of a 1N sodium hydroxide aqueous solution and then 3 times with 100 ml of water and then dried over anhydrous sodium sulfate. The solvent was distilled off and the resulting residue was recrystallized from methanol to give 1.3 g of (S)-(+)-α-(3,4-dihydro-6-carbostyril)-acetone glycerol as white crystals having a melting point of 146° − 148° C and $[\alpha]_D^{21} = +5.3$ (c=0.9, CHCl₃).

REFERENCE EXAMPLE 4

0.9 g of 6-hydroxy-3,4-dihydrocarbostyril and 0.35 g of sodium ethylate were added to 4.5 ml of 2-methoxyethanol, and the mixture was refluxed for 10 minutes. To the resulting mixture was then added a solution of 1.5 g of (S)-(+)-α-(p-toluenesulfonyl)acetone glycerol dissolved in 7.5 ml of 2-methoxyethanol, and the mixture was refluxed for 3 hours. After allowing the mixture to cool, the solvent was distilled off under reduced pressure. The residue thus obtained was shaken with 50 ml of chloroform and 50 ml of a 1N sodium hydroxide aqueous solution, and the organic layer was separated, washed with 50 ml of a 1N sodium hydroxide aqueous solution and then 3 times with 50 ml of water and then dried over anhydrous sodium sulfate. The solvent was distilled off and the resulting residue was recrystallized from methanol to give 0.6 g of (R)-(−)-α-(3,4-dihydro-6-carbostyril)acetone glycerol as white crystals having a melting point of 145° − 146° C and $[\alpha]_D^{21} = -5.3°$ (c=0.9, CHCl₃).

REFERENCE EXAMPLE 5

1.8 g of 7-hydroxy-3,4-dihydrocarbostyril and 0.7 g of sodium ethylate dissolved in 9 ml of 2-methoxyethanol, and 3.0 g of (R)-(−)-α-(p-toluenesulfonyl)acetone glycerol dissolved in 15 ml of 2-methoxyethanol were treated in the same manner as described in Reference Example 3. The solvent was distilled off to give a syrup which was then crystallized from diethyl ether. The crude crystals thus obtained were recrystallized from methanol to give 1.8 g of (S)-(+)-α-(3,4-dihydro-7-carbostyril)acetone glycerol as white crystals having a melting point of 114° − 115° C and $[\alpha]_D^{21} = +5.6°$ (c=1.1, CHCl₃).

REFERENCE EXAMPLE 6

0.9 g of 7-hydroxy-3,4-dihydrocarbostyril and 0.35 g of sodium ethylate dissolved in 4.5 ml of 2-methoxyethanol, and 1.5 g of (S)-(+)-α-(p-toluenesulfonyl)acetone glycerol dissolved in 15 ml of 2-methoxyethanol were treated in the same manner as described in Reference Example 3, and the resulting residue was recrystallized from methanol to give 0.45 g of (R)-(−)-α-(3,4-dihydro-7-carbostyril)acetone glycerol as white crystals having a melting point of 114° − 116° C and $[\alpha]_D^{21} = -5.3°$ (c=0.7, CHCl₃).

REFERENCE EXAMPLE 7

2.4 g of 8-hydroxy-3,4-dihydrocarbostyril and 0.9 g of sodium ethylate dissolved in 12 ml of 2-methoxyethanol, and 4.0 g of (R)-(−)-α-(p-toluenesulfonyl)acetone glycerol dissolved in 20 ml of 2-methoxyethanol were treated in the same manner as described in Reference Example 3. The solvent was distilled off to give a syrup which was then crystallized from diethyl ether. The crystals thus obtained were recrystallized from methanol to give 1.4 g of (S)-(+)-α-(3,4-dihydro-8-carbostyril)-acetone glycerol as white crystals having a melting point of 108° − 109° C and $[\alpha]_D^{21} = +5.5°$ (c=0.9, CHCl₃).

REFERENCE EXAMPLE 8

0.9 g of 8-hydroxy-3,4-dihydrocarbostyril and 0.35 g of sodium ethylate dissolved in 4.5 ml of 2-methoxyethanol, and 1.5 g of (S)-(+)-α-(p-toluenesulfonyl)acetone glycerol dissolved in 15 ml of 2-methoxyethanol were treated in the same manner as described in Reference Example 3, and the resulting residue was recrystallized from methanol to give 0.4 g of (R)-(−)-α-(3,4-dihydro-8-carbostyril)acetone glycerol as white crystals having a melting point of 109° − 110° C and $[\alpha]_D^{21} = +5.4°$ (c=0.8, CHCl₃).

EXAMPLE 16

4.5 ml of an 80% acetic acid aqueous solution was added to 900 mg of (S)-(+)-α-(3,4-dihydro-6-carbostyril)acetone glycerol prepared in Reference Example 3, and the mixture was heated at a bath temperature of 55° to 60° C for 30 minutes. After allowing the mixture to cool, 45 ml of diethyl ether was added to the mixture followed by cooling. The precipitated crystals were filtered, washed with diethyl ether and recrystallized from ethanol to give 400 mg of (R)-(−)-α-(3,4-dihydro-6-carbostyril)glycerol as white crystals having a melting point of 168° − 169° C and $[\alpha]_D^{21} = -7.9°$ (c=0.6, dimethyl sulfoxide).

EXAMPLE 17

500 mg of (R)-(−)-α-(3,4-dihydro-6-carbostyril)acetone glycerol prepared in Reference Example 4 and 2.5 ml of an 80% acetic acid aqueous solution were treated in the same manner as described in Example 16 to give 200 mg of (S)-(+)-α(3,4-dihydro-6-carbostyril)glycerol as white ccrystals having a melting point of 169° - 170° C and $[\alpha]_D^{21} = +8.2°$ (c=0.9, dimethyl sulfoxide).

EXAMPLE 18

600 mg of (S)-(+)-α-(3,4-dihydro-7-carbostyril)acetone glycerol prepared in Reference Example 5 and 3 ml of an 80% acetic acid aqueous solution were treated in the same manner as described in Example 16, and the resulting residue was recrystallized from a mixture of ethanol and diethyl ether to give 200 mg of (R)-(−)-α-(3,4-dihydro-7-carbostyril)glycerol as white crystals having a melting point of 126° - 127° C and $[\alpha]_D^{21} = -8.7°$ (c=0.6, ethanol).

EXAMPLE 19

400 mg of (R)-(−)-α-(3,4-dihydro-7-carbostyril)acetone glycerol prepared in Reference Example 6 and 2 ml of an 80% acetic acid aqueous solution were treated in the same manner as described in Example 16 to give 200 mg of (S)-(+)-α-(3,4-dihydro-7-carbostyril)glycerol as white crystals having a melting point of 125° - 126° C and $[\alpha]_D^{21} = +9.0°$ (c=0.5, ethanol).

EXAMPLE 20

7.0 g of (S)-(+)-α-(3,4-dihydro-8-carbostyril)acetone glycerol prepared in Reference Example 7 and 35 ml of 80% acetic acid were treated in the same manner as described in Example 16 to give 3.4 g of (R)-(−)-α-(3,4-dihydro-8-carbostyril)glycerol as white crystals having a melting point of 182° - 183° C and $[\alpha]_D^{21} = -39.7°$ (c=1.1, dimethyl sulfoxide).

EXAMPLE 21

500 mg of (R)-(−)-α-(3,4-dihydro-8-carbostyril)acetone glycerol prepared in Reference Example 8 and 2.5 ml of an 80% acetic acid aqueous solution were treated in the same manner as described in Example 16 to give 200 mg of (S)-(+)-α-(3,4-dihydro-8-carbostyril)glycerol as white crystals having a melting point of 182° - 184° C and $[\alpha]_D^{21} = +39.0°$ (c=1.2, dimethyl sulfoxide).

EXAMPLE 22

16 g of 5-hydroxyisocarbostyril was dissolved in 110 ml of a 1N aqueous sodium hydroxide solution, and 8 g of glycidol was added to the solution. The mixture was then refluxed for 2 hours while stirring. After allowing the mixture to cool, the precipitated crystals were filtered, and recrystallized from water to give 20 g of 5-(2,3-dihydroxy)propoxyisocarbostyril as colorless needle-like crystals having a melting point of 228° - 230° C.

EXAMPLE 23

To 100 ml of ethanol in which 2,5 g of sodium metal had been dissolved was added 15 g of 8-hydroxyquinoline. 12 g of epichlorohydrin was then added to the resulting solution and the mixture was refluxed for 8 hours while stirring. After completion of the reaction, the precipitated material was removed by filtration, and the mother liquor was concentrated to dryness. The resulting residue was recrystallized from ethanol-water to give 16 g of 8-(2,3-dihydroxy)propoxyquinoline as colorless needle-like crystals having a melting point of 193° - 194° C.

In the same manner as described in Example 22 and 23, the following compounds were prepared from the appropriate starting materials.

| Procedure (Example No.) | Starting Material | Compound | Recrystallization Solvent | Melting Point (° C) | Appearance |
|---|---|---|---|---|---|
| 22 | [structure] | [structure] | Ethanol | 223 - 225 | Colorless Plate-like |
| 22 | [structure] | [structure] | Water | 182 - 183 | Colorless Needle-like |
| 22 | [structure] | [structure] | Ethanol | 119.5 - 121 | Colorless Amorphous |
| 22 | [structure] | [structure] | Ligroin | 101 - 102.5 | Colorless Needle-like |

-continued

| Procedure (Example No.) | Starting Material | Compound | Recrystallization Solvent | Melting Point (° C) | Appearance |
|---|---|---|---|---|---|
| 23 | [structure: 4-methyl-8-hydroxy quinolinone] | [structure: 4-methyl-8-(2,3-dihydroxypropoxy) quinolinone] | Ethanol-Water | 223 – 226 | Colorless Amorphous |
| 23 | [structure: 4-methyl-6-hydroxy-1-methyl quinolinone] | [structure: 4-methyl-6-(2,3-dihydroxypropoxy)-1-methyl quinolinone] | Ethanol n-Hexane | 160 – 163 | Colorless Amorphous |
| 23 | [structure: 5-hydroxy quinolinone] | [structure: 5-(2,3-dihydroxypropoxy) quinolinone] | Ethanol | 210 – 214 | Colorless Amorphous |

As described previously, the compounds of this invention possess an inhibitory activity on platelet aggregation. The inhibitory activity of some compounds of this invention and the method for determination of the activity are described hereinafter in greater detail.

The aggregation inhibitory activity was determined using an AG-II type aggregometer (made by Bryston Manufacturing Co.). A blood sample was withdrawn from rabbits as a mixture of sodium citrate and whole blood in a proportion of 1:9 by volume and centrifuged at 1000 rpm for 10 minutes to obtain a platelet rich plasma (PRP). The resulting PRP was separated, and the remaining blood sample was further centrifuged at 3000 rpm for 15 minutes to obtain a platelet poor plasma (PPP).

The number of platelets in the PRP was counted in accordance with the Brecher-Clonkite Method, and the PRP was diluted with the PPP to prepare a PRP sample containing platelets in an amount of 300,000/mm$^3$ for an adenosine diphosphate (ADP)-induced aggregation test and a PRP sample containing platelets in an amount of 450,000/mm$^3$ for a collagen-induced aggregation test.

0.01 ml of a solution of a test compound having a predetermined concentration (as shown in the Tables below) was then added to 0.6 ml of the PRP sample obtained above and the mixture was incubated at a temperature of 37° C for 1 minute. Then 0.07 ml of an ADP or collagen solution was added to the mixture. The mixture was then subjected to a transmittance determination and changes in the transmittance of the mixture were recorded using aggregometer at a stirrer rotation rate of 1100 rpm. In this test, Owren Veronal buffer (pH 7.35) was used for the preparation of solutions of ADP, collgen and the test compounds. ADP was adjusted to a concentration of $7.5 \times 10^{-5}$M, and the collagen solution was prepared by triturating 100 mg of collagen with 5 ml of the above buffer and the supernatant obtained was used as a collagen inducer. Adenosine and acetylsalicylic acid were used as controls for the ADP-induced aggregation test and the collagen-induced aggregation test, respectively. The aggregation inhibitory activity was determined in terms of the percent inhibition (%) with respect to the aggregation ratio of controls. The aggregation ratio can be calculated by the following equation:

$$\text{Aggregation Ratio} = \frac{c-a}{b-a} \times 100$$

Wherein:
"a" is the optical density of the PRP,
"b" is the optical density of the PRP having incorporated therein a test compound and an aggregation inducer, and
"c" is the optical density of the PPP.

| Inhibition of Collagen-Induced Aggregation In Rabbit Platelets (Inhibition %) | | | |
|---|---|---|---|
| | Concentration | | |
| Compound | $10^{-8}$M | $10^{-6}$M | $10^{-4}$M |
| [structure: 5-(2,3-dihydroxypropoxy)-3,4-dihydroquinolinone] | 8 | 11 | 100 |

-continued
Inhibition of Collagen-Induced Aggregation In Rabbit Platelets (Inhibition %)

| Compound | Concentration | | |
|---|---|---|---|
| | $10^{-8}$M | $10^{-6}$M | $10^{-4}$M |
| 8-(2,3-dihydroxypropoxy)-1-methyl-3,4-dihydrocarbostyril | 0 | 13 | 7 |
| 5-(2,3-dihydroxypropoxy)-1-allyl-3,4-dihydrocarbostyril | 0 | 0 | 0 |
| 5-(2,3-dihydroxypropoxy)-3,4-dihydrocarbostyril | 26 | 9 | 100 |
| 7-(2,3-dihydroxypropoxy)-3,4-dihydrocarbostyril | 4 | 18 | 13 |
| 8-(2,3-dihydroxypropoxy)-3,4-dihydrocarbostyril | 21 | 7 | 25 |

Inhibition of ADP-Induced Aggregation In Rabbit Platelets (Inhibition %)

| Compound | Concentration | | |
|---|---|---|---|
| | $10^{-8}$M | $10^{-6}$M | $10^{-4}$M |
| 8-(2,3-dihydroxypropoxy)-3,4-dihydrocarbostyril | 21 | 17 | 21 |
| 8-(2,3-dihydroxypropoxy)-1-methyl-3,4-dihydrocarbostyril | 0 | 13 | 7 |
| 5-(2,3-dihydroxypropoxy)-1-allyl-3,4-dihydrocarbostyril | 0 | 0 | 0 |
| 5-(2,3-dihydroxypropoxy)-3,4-dihydrocarbostyril | 26 | 9 | 100 |
| 7-(2,3-dihydroxypropoxy)-3,4-dihydrocarbostyril | 4 | 18 | 13 |
| 8-(2,3-dihydroxypropoxy)-3,4-dihydrocarbostyril | 21 | 7 | 25 |
| | 10 | 13 | 2 |

-continued

| Inhibition of ADP-Induced Aggregation In Rabbit Platelets (Inhibition %) | | | |
|---|---|---|---|
| | Concentration | | |
| Compound | $10^{-8}M$ | $10^{-6}M$ | $10^{-4}M$ |
| 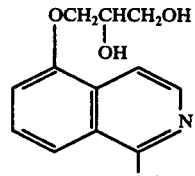 | 0 | 6 | 2 |
| Adenosine | 5 | 47 | 70 |

| Inhibition of ADP-Induced Aggregation In Rabbit Platelets (Inhibition %) | | | | |
|---|---|---|---|---|
| | Concentration | | | |
| Compound | $10^{-8}M$ | $10^{-6}M$ | $10^{-5}M$ | $10^{-4}M$ |
| 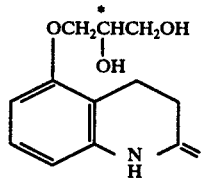[R-(−)-isomer] | 0 | 8 | 16 | 49 |
| 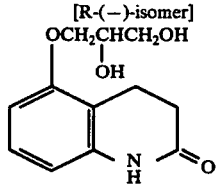 | 15 | 18 | 18 | 51 |
| Adenosine | 15 | 63 | 74 | 92 |

| Inhibition of Collagen-Induced Aggregation In Rabbit Platelets (Inhibition %) | | | | |
|---|---|---|---|---|
| | Concentration | | | |
| Compound | $10^{-8}M$ | $10^{-6}M$ | $10^{-5}M$ | $10^{-4}M$ |
| 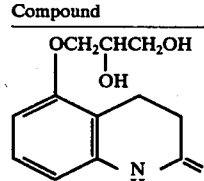[R-(−)-isomer] | 0 | 3 | 3 | 95 |
| 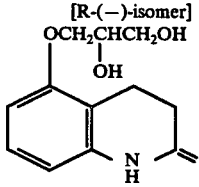 | 3 | 7 | 17 | 95 |
| Acetylsalicylic Acid | — | 8 | 12 | 100 |

While the invention has been described in detail and with reference to specific embodiments thereof, it will be apparent to one skilled in the art that various changes and modifications can be made therein without departing from the spirit and scope thereof.

What is claimed is:

1. A glycerol derivative represented by the formula

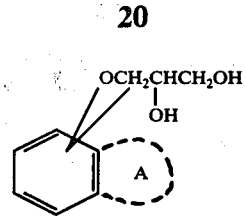

wherein A represents the atoms necessary to complete a bicyclic ring selected from the group consisting of

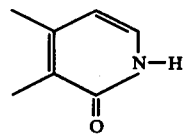

wherein R represents a hydrogen atom, an alkyl group having 1 to 4 carbon atoms, an alkenyl group having 2 to 4 carbon atoms or a phenylalkyl group having 1 or 2 carbon atoms in the alkyl moiety thereof; and the optically active isomers thereof.

2. 1-Benzyl-5-(2,3-dihydroxy)propoxy-3,4-dihydrocarbostyril according to claim 1.

3. 1-Methyl-5-(2,3-dihydroxy)propoxy-3,4-dihydrocarbostyril according to claim 1.

4. 1-Ethyl-5-(2,3-dihydroxy)propoxy-3,4-dihydrocarbostyril according to claim 1.

5. 1-Allyl-5-(2,3-dihydroxy)propoxy-3,4-dihydrocarbostyril according to claim 1.

6. 5-(2,3-Dihydroxy)propoxy-3,4-dihydrocarbostyril according to claim 1.

7. 1-Benzyl-5-(2,3-dihydroxy)propoxy-3,4-dihydrocarbostyril according to claim 1.

8. 8-(2,3-Dihydroxy)propoxy-3,4-dihydrocarbostyril according to claim 1.

9. 6-(2,3-Dihydroxy)propoxy-3,4-dihydrocarbostyril according to claim 1.

10. 7-(2,3-Dihydroxy)propoxy-3,4-dihydroxycarbostyril according to claim 1.

11. (R)-(−)-α-(3,4-Dihydro-5-carbostyril)glycerol according to claim 1.

12. (S)-(+)-α-(3,4-Dihydro-5-carbostyril)glycerol according to claim 1.

13. (R)-(−)-α-(3,4-Dihydro-6-carbostyril)glycerol according to claim 1.

14. (S)-(+)-α-(3,4-Dihydro-6-carbostyril)glycerol according to claim 1.

15. (R)-(−)-α-(3,4-Dihydro-7-carbostyril)glycerol according to claim 1.

16. (S)-(+)-α-(3,4-Dihydro-7-carbostyril)glycerol according to claim 1.

17. (R)-(−)-α-(3,4-Dihydro-8-carbostyril)glycerol according to claim 1.

18. (S)-(−)-α-(3,4-Dihydro-8-carbostyril)glycerol according to claim 1.

19. 5-(2,3-Dihydroxy)propoxyisocarbostyril according to claim 1.

20. 8-(2,3-Dihydroxy)propoxyquinoline according to claim 1.

21. 1,4-Dimethyl-6-(2,3-dihydroxy)propoxycarbostyril according to claim 1.

22. 5-(2,3-Dihydroxy)propoxycarbostyril according to claim 1.

23. The glycerol derivative according to claim 1, wherein the bicyclic ring to be completed by A is

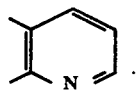

24. The glycerol derivative according to claim 1, wherein the bicyclic ring to be completed by A is

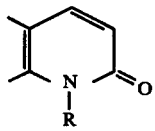

wherein R represents a hydrogen atom, an alkyl group having 1 to 4 carbon atoms, an alkenyl group having 2 to 4 carbon atoms or a phenylalkyl group having 1 or 2 carbon atoms in the alkyl moiety thereof.

25. The glycerol derivative according to claim 1, wherein the bicyclic ring to be completed by A is

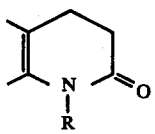

wherein R represents a hydrogen atom, an alkyl group having 1 to 4 carbon atoms, an alkenyl group having 2 to 4 carbon atoms or a phenylalkyl group having 1 or 2 carbon atoms in the alkyl moiety thereof.

26. The glycerol derivative according to claim 1, wherein the bicyclic ring to be completed by A is

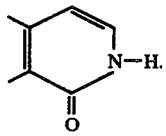

27. The glycerol derivative according to claim 1, wherein the bicyclic ring to be completed by A is

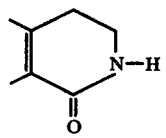

28. The glycerol derivative according to claim 1, wherein the bicyclic ring to be completed by A is

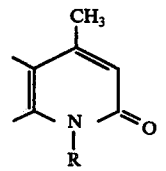

wherein R represents a hydrogen atom, an alkyl group having 1 to 4 carbon atoms, an alkenyl group having 2 to 4 carbon atoms or a phenylalkyl group having 1 or 2 carbon atoms in the alkyl moiety thereof.

* * * * *

UNITED STATES PATENT AND TRADEMARK OFFICE
CERTIFICATE OF CORRECTION

PATENT NO. : 4,065,456
DATED : December 27, 1977
INVENTOR(S) : Kazuyuki NAKAGAWA et al It is certified that error appears in the above-identified patent and that said Letters Patent are hereby corrected as shown below:

IN THE HEADING:

FOREIGN APPLICATION PRIORITY DATA:

Insert: -- October 9, 1974   Japan ........ 49-116419   --.

Signed and Sealed this

Fourth Day of April 1978

[SEAL]

Attest:

RUTH C. MASON
Attesting Officer

LUTRELLE F. PARKER
Acting Commissioner of Patents and Trademarks